(12) United States Patent
Poland et al.

(10) Patent No.: US 11,759,168 B2
(45) Date of Patent: Sep. 19, 2023

(54) ULTRASOUND VASCULAR NAVIGATION DEVICES AND METHODS

(71) Applicant: KONINKLIJKE PHILIPS N.V., Eindhoven (NL)

(72) Inventors: Mckee Dunn Poland, Andover, MA (US); Nico Maris Adriaan de Wild, Eindhoven (NL); Franciscus Hendrikus van Heesch, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/764,031

(22) PCT Filed: Nov. 5, 2018

(86) PCT No.: PCT/EP2018/080105
§ 371 (c)(1),
(2) Date: May 14, 2020

(87) PCT Pub. No.: WO2019/096599
PCT Pub. Date: May 23, 2019

(65) Prior Publication Data
US 2020/0359990 A1 Nov. 19, 2020

Related U.S. Application Data

(60) Provisional application No. 62/585,611, filed on Nov. 14, 2017.

(51) Int. Cl.
*A61B 8/08* (2006.01)
*A61B 8/06* (2006.01)
(Continued)

(52) U.S. Cl.
CPC ............... *A61B 8/085* (2013.01); *A61B 8/06* (2013.01); *A61B 8/14* (2013.01); *A61B 8/4254* (2013.01);
(Continued)

(58) Field of Classification Search
CPC ......... A61B 8/085; A61B 8/0891; A61B 8/06; A61B 8/14; A61B 8/4254; A61B 8/4472;
(Continued)

(56) References Cited

U.S. PATENT DOCUMENTS 4,289,139 A 9/1981 Enjoji et al.
5,259,386 A 11/1993 Sharkawy
(Continued)

FOREIGN PATENT DOCUMENTS

GB 2400176 A * 10/2004 ......... A61B 17/3403
GB 2400176 A 10/2004
(Continued)

OTHER PUBLICATIONS

International Search Report and Written Opinion for International Application No. PCT/EP2018/080105, filed Nov. 5, 2018, 14 pages.
(Continued)

*Primary Examiner* — Patricia J Park
*Assistant Examiner* — Adil Partap S Virk

(57) ABSTRACT

Ultrasound image devices, systems, and methods are provided. In one embodiment, an ultrasound device includes a first ultrasound component (210) configured to generate a first signal representative of a subject's anatomy along a first axis; a second ultrasound component (220) configured to generate a second signal representative of the subject's anatomy along a second axis, the first axis disposed at an angle with respect to the second axis; and a processing component (420) in communication with the first ultrasound component and the second ultrasound component, the pro- (Continued)

cessing component configured to determine an orientation of the ultrasound device with respect to the subject's anatomy based on the first signal and the second signal. In one embodiment, the processing component is further configured to indicate, via visual indicators (132, 240) on the ultrasound device, a direction to orient the ultrasound device based on the determined orientation for aligning the ultrasound device with the subject's anatomy.

19 Claims, 11 Drawing Sheets

(51) Int. Cl.
*A61B 8/14* (2006.01)
*A61B 8/00* (2006.01)

(52) U.S. Cl.
CPC .......... *A61B 8/4472* (2013.01); *A61B 8/4477* (2013.01); *A61B 8/4488* (2013.01); *A61B 8/463* (2013.01); *A61B 8/488* (2013.01); *A61B 8/54* (2013.01); *A61B 8/56* (2013.01)

(58) Field of Classification Search
CPC ..... A61B 8/4477; A61B 8/4488; A61B 8/463; A61B 8/488; A61B 8/54; A61B 8/56; A61B 8/42; A61B 8/4245; A61B 8/145; A61B 8/0841
See application file for complete search history.

(56) References Cited

U.S. PATENT DOCUMENTS

| | | | |
|---|---|---|---|
| 5,769,079 A | 6/1998 | Hossack | |
| 6,139,496 A * | 10/2000 | Chen | A61B 8/4444 600/459 |
| 6,251,073 B1 * | 6/2001 | Imran | A61B 8/4209 600/443 |
| 6,261,233 B1 * | 7/2001 | Kantorovich | A61B 8/06 600/454 |
| 9,439,653 B2 | 9/2016 | Avneri et al. | |
| 2006/0042389 A1 * | 3/2006 | Sato | A61B 8/145 73/603 |
| 2006/0211942 A1 * | 9/2006 | Hoctor | A61B 8/4236 600/438 |
| 2009/0275823 A1 | 11/2009 | Ayati et al. | |
| 2010/0210946 A1 * | 8/2010 | Harada | A61B 8/4281 600/443 |
| 2010/0312120 A1 * | 12/2010 | Meier | A61B 8/00 600/459 |
| 2014/0088430 A1 | 3/2014 | Poland | |
| 2015/0032004 A1 | 1/2015 | Kim et al. | |
| 2015/0065916 A1 | 3/2015 | Maguire et al. | |
| 2015/0126865 A1 * | 5/2015 | Murai | A61B 8/0891 600/437 |
| 2016/0000408 A1 * | 1/2016 | Matsunaga | A61B 8/5223 600/441 |
| 2016/0374644 A1 * | 12/2016 | Mauldin, Jr. | A61B 8/085 600/424 |
| 2020/0187981 A1 * | 6/2020 | Tian | A61B 8/4494 |

FOREIGN PATENT DOCUMENTS

| | | |
|---|---|---|
| JP | 2006115986 A | 5/2006 |
| JP | 2009045427 A | 3/2009 |
| WO | 2017156023 A1 | 9/2017 |

OTHER PUBLICATIONS

Luminetx VeinViewer, The Future of Things, 1 page (Abstract).
AccuVein AV300, Vein Illumination Device, Facts Sheet, 2 pages (Abstract).

* cited by examiner

ULTRASOUND VASCULAR NAVIGATION DEVICES AND METHODS

RELATED APPLICATIONS

This application is the U.S. National Phase application under 35 U.S.C. § 371 of International Application No. PCT/EP2018/080105, filed on Nov. 5, 2018, which claims the benefit of and priority to Provisional Application No. 62/585,611, filed Nov. 14, 2017. These applications are incorporated by reference herein.

TECHNICAL FIELD

The present disclosure relates generally to ultrasound scanning, in particular, to providing vascular navigational information for medical vascular access procedures. For example, an ultrasound scanning device can include ultrasound sensors arranged to provide bi-plane image signals with orthogonal lateral resolutions. The ultrasound scanning device can locally process the bi-plane image signals to identify a blood vessel for receiving a venipuncture and guide a clinician to align the ultrasound scanning device with the blood vessel.

BACKGROUND

Treating or diagnosing certain diseases often requires obtaining intravenous accesses for intravenous therapy or for blood sampling of venous bloods. For example, a clinician may make a venipuncture with a cannula to access a patient's vein. For blood sampling, the clinician may insert a needle into the patient's vessel to draw blood for sampling. For intravenous therapy, the clinician may thread a catheter through the patient's vessel to a desired location to deliver fluid, blood, medications, or treatments to the patient. A clinician may begin a venipuncture procedure by identifying a suitable vessel on a patient for the venipuncture. Currently, a clinician may locate a puncture site through visual inspection and/or palpation. In some instances, additional real-time imaging may be used to guide an intravenous access procedure. For example, real-time images tracking the insertion process of a needle within the patient's body may be displayed on a monitor to guide a clinician in carrying out the intravenous access procedure.

The efficiency, accuracy, or safety of an intravenous access procedure may be critical especially during an emergency. However, emergency settings may increase the obstacles in obtaining successful intravenous accesses. For example, environmental factors may impede the visibility of a patient's vein. In addition, patient factors such as the collapse of a patient's vein due to shock may cause palpation to fail in locating the patient's vein. Further, real-time imaging equipment may not be readily accessible in an emergency situation.

SUMMARY

While existing procedures for locating a puncture site have proved useful for intravenous accesses, there remains a clinical need for improved systems and techniques for providing efficient, accurate, and safe procedures for intravenous accesses. Embodiments of the present disclosure provide an integrated, autonomous ultrasound vascular navigation device. The vascular navigation device may include a first ultrasound component and a second ultrasound that can provide bi-plane image signals with orthogonal lateral resolutions. The vascular navigation device can be placed on a surface of a patient's body part (e.g., arms, legs, or back). The navigation device can identify a major blood vessel in the patient's body part and guide a clinician to align the navigation device to the blood vessel based on the image signals. For example, the navigation device can include visual indicators indicating directions to orient the navigation device. After the alignment, the clinician may accurately insert a needle or any medical device into the blood vessel. For example, the navigation device can include visual alignment markers indicating a location directly above the identified blood vessel.

In one embodiment, an ultrasound device includes a first ultrasound component configured to generate a first signal representative of a subject's anatomy along a first axis; a second ultrasound component configured to generate a second signal representative of the subject's anatomy along a second axis, the first axis disposed at an angle with respect to the second axis; and a processing component in communication with the first ultrasound component and the second ultrasound component, the processing component configured to determine an orientation of the ultrasound device with respect to the subject's anatomy based on the first signal and the second signal.

In some embodiments, the first axis is orthogonal to the second axis. In some embodiments, the first ultrasound component includes an array of ultrasound transducer elements. In some embodiments, the processing component is further configured to determine Doppler measures based on the first signal and the second signal; and determine the orientation based on the Doppler measures. In some embodiments, the processing component is further configured to determine signal intensity measures based on the first signal and second signal; and determine the orientation based on the signal intensity measures. In some embodiments, the ultrasound device further comprises one or more visual indicators in communication with the processing component, wherein the processing component is further configured to indicate, via the one or more visual indicators, a direction to orient the ultrasound device based on the determined orientation such that an axis of the ultrasound device is aligned with the subject's anatomy. In some embodiments, the one or more visual indicators include an arrow. In some embodiments, the subject's anatomy includes a blood vessel, and wherein the processing component is further configured to determine that the axis of the ultrasound device is aligned with an axis of blood flow in the blood vessel; and indicate, via the one or more visual indicators, an alignment completion in response to determining that the axis of the ultrasound device is aligned with the axis of blood flow in the blood vessel. In some embodiments, the ultrasound device further comprises a top plane; a bottom plane opposite the top plane; and an opening extending through the ultrasound device from the top plane to the bottom plane, the opening aligned with the axis of the ultrasound device and configured to receive a medical device for insertion into the blood vessel. In some embodiments, the first ultrasound component and the second ultrasound component are spatially separated by the opening. In some embodiments, the ultrasound device further comprises a communication interface in communication with the processing component and a remote device, the communication interface configured to transmit the first signal and the second signal to the remote device for displaying an image of the subject's anatomy based on at least one of the first signal or the second signal. In some embodiments, the processing component is further configured to receive, via the communication interface, a control signal for configuring at least one of the first ultrasound component or the second ultrasound component. In some embodiments, the communication interface is a wireless link.

In one embodiment, a method of ultrasound scanning includes generating, by a first ultrasound component of an ultrasound device, a first signal representative of a subject's anatomy along a first axis; generating, by a second ultrasound component of the ultrasound device, a second signal representative of the subject's anatomy along a second axis, the first axis disposed at an angle with respect to the second axis; and determining an orientation of the ultrasound device with respect to the subject's anatomy based on the first signal and the second signal.

In some embodiments, the first axis is orthogonal to the second axis. In some embodiments, the generating the first signal includes beamforming a plurality of ultrasound echo signals received from an array of ultrasound transducers of the first ultrasound component. In some embodiments, the method further comprises determining at least one of Doppler measures or intensity measures based on the first signal and the second signal; and determining the orientation based on the at least one of Doppler measures or intensity measures. In some embodiments, the method further comprises indicating, via one or more visual indicators, a direction to orient the ultrasound device based on the determined orientation such that an axis of the ultrasound device is aligned with the subject's anatomy. In some embodiments, the subject's anatomy includes a blood vessel, wherein the method further comprises determining that an axis of the ultrasound device is aligned with an axis of blood flow in the blood vessel; and indicating, via one or more visual indicators, an alignment completion in response to determining that the axis of the ultrasound device is aligned with the axis of blood flow in the blood vessel. In some embodiments, the method further comprises transmitting the first signal and the second signal to a remote device; and displaying an image of the subject's anatomy based on at least one of the first signal or the second signal.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
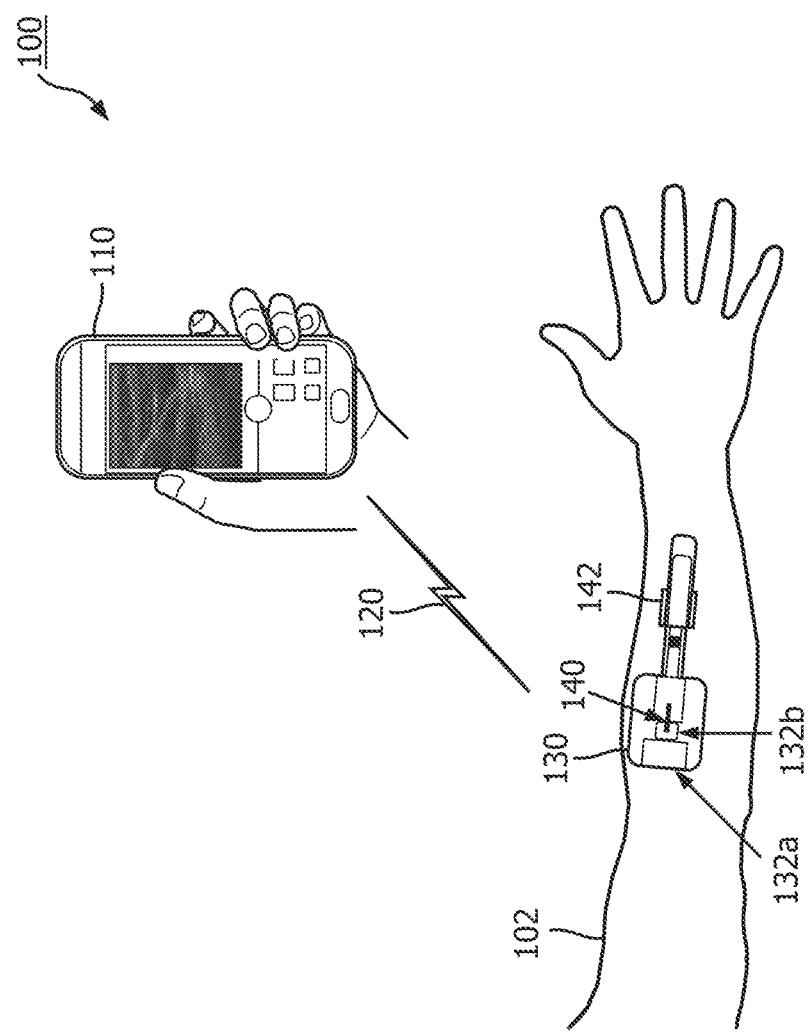
FIG. 1 is a schematic diagram of a vascular navigation system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of a vascular navigation system 100, according to aspects of the present disclosure. The system 100 may include an ultrasound scanning device 130. At a high level, the ultrasound scanning device 130 may operate as a vascular compass, allowing a clinician to locate a vessel for an intravenous access procedure. The ultrasound scanning device 130 may include ultrasound sensors or transducer elements configured to emit ultrasonic energy towards a patient's anatomy. The ultrasonic energy is reflected by the patient's vasculatures and/or tissue structures under scanning. The ultrasound transducer elements in the ultrasound scanning device 130 may receive the reflected ultrasound echo signals. The ultrasound scanning device 130 may include an internal or integrated processing component that can process the ultrasound echo signals locally to generate image signals representative of the patient's anatomy under the scanning. The ultrasound sensors can be arranged to provide bi-plane image signals with orthogonal lateral resolutions. For example, the bi-plane image signals can provide a lateral view and a transverse view of a blood vessel. The bi-plane image signals may be in the form of signal intensity measures (e.g., brightness) or flow measures (e.g., Doppler-shifts).

The ultrasound scanning device 130 may identify a blood vessel (e.g., a major vessel or a large vessel) in the patient's anatomy under the scanning and determine an orientation of the ultrasound scanning device 130 with respect to the vessel based on the bi-plane image signals. The ultrasound scanning device 130 may process and analyze the bi-plane image signals. The ultrasound scanning device 130 may direct a clinician to orient (e.g., rotate or shift in a range of positions) the ultrasound scanning device 130 such that the ultrasounds scanning device 130 is aligned with the vessel. In some instances, the processing, the analysis, and the orienting may be repeated over multiple iterations.

In an embodiment, the ultrasound scanning device 130 may employ visual directional indicators to guide a clinician in moving (e.g., sliding and/or rotating) the ultrasound scanning device 130 in certain directions and/or positions. When the ultrasound scanning device 130 is aligned with the vessel, the ultrasound scanning device 130 may indicate the completion of the alignment and/or a position for inserting a needle 140. The ultrasound scanning device 130 may employ visual alignment indicators 132 to indicate the alignment completion and/or a needle insertion position.

The visual alignment indicators 132 may include light-emitting diodes (LEDs) or any illuminable elements that can be activated or deactivated. The visual alignment indicators 132 are shown as 132a and 132b. The visual alignment indicator 132a may be located at an edge of the ultrasound scanning device 130 and may be triangular in shape marking a position where the needle 140 may be inserted. The visual alignment indicator 132b may surround the rim of an opening on the ultrasound scanning device 130. The opening may extend through the ultrasound scanning device 130 allowing a needle 140 to be inserted into the vessel through the opening. Techniques for processing and analyzing the echo data and configurations for the ultrasound transducers, the visual directional indicators, and the visual alignment indicators 132 are described in greater detail herein. In operation, a clinician may place the ultrasound scanning device 130 on a patient at an approximate site that has been prepared for venipuncture or peripheral inserted central catheter (PICC). The approximate site may be a patient's arm 102 as shown or any other body parts, such as a patient's leg or back. The clinician may move the ultrasound scanning device 130 around the approximate site until the ultrasound scanning device 130 detects a desired blood vessel (e.g., a major vessel or a large vessel) for a venipuncture. The ultrasound scanning device 130 may direct (e.g., via visual indicators) the clinician to slide and/or rotate the ultrasound scanning device 130 into a final position for the venipuncture. In the final position, the locations of the visual alignment indicators 132 may be directly above blood vessel. Thus, the clinician may insert the needle 140 through the opening as shown in FIG. 1. Alternatively, the clinician may insert the needle 140 at the edge of the ultrasound scanning device 130 where the visual alignment indicator 132a is located. After the insertion, the clinician may remove the ultrasound scanning device 130 and the ultrasound scanning device 130 may be sterilized.

The system 100 may optionally include a remote image processing and display device 110 in communication with the communication link 120. The remote image processing and display device 110 may be any suitable computing device with a display. For example, the remote image processing and display device 110 may be a mobile device or a tablet. The ultrasound scanning device 130 may transmit the collected echo signals and/or processed echo signals (e.g., image signals) to the remote image processing and display device 110 for real-time image display. The communication link 120 may be a wireless link as shown or any other suitable communication link, for example, capable of supporting a data transfer rate of about 2 megabits per second (Mbit/sec) and an image frame rate of about 5 hertz (Hz) to provide a sufficient resolution. In some embodiments, the communication link 120 may be a low-power Bluetooth® version 5 wireless link. The remote image processing and display device 110 may be configured to provide a longitudinal vessel view or a transverse vessel view. In an embodiment, the remote image processing and display device 110 may provide a simultaneous bi-plane view (e.g., at a half frame rate) to allow a real-time view of both a needle-in-vessel in one direction and the vessel in an orthogonal direction.

In an embodiment, the system 100 may optionally provide a needle insertion confirmation for an intravenous access. For example, the system 100 may further include a mobile pulse detection module (PDM) in communication with the needle 140 and the ultrasound scanning device 130. The ultrasound scanning device 130 may encapsulate location information associated with the tip of the needle 140 with image data and transmit the needle tip information along with the image data to the remote image processing and display device 110. Some examples of needle tip location tracking systems are described in U.S. Pat. App. Pub. No. US20160317119, titled "SYSTEM AND METHOD FOR TRACKING A PENETRATING INSTRUMENT," U.S. Pat. App. Pub. No. US20150119701, titled "ULTRASONIC IMAGING APPARATUS AND A METHOD FOR IMAGING A SPECULAR OBJECT AND A TARGET ANATOMY IN A TISSUE USING ULTRASOUND," and International Pat. Appl. Pub. No. WO2012172458, titled "THREE-DIMENSIONAL NEEDLE LOCALIZATION WITH A TWO-DIMENSIONAL IMAGING PROBE", each of which is hereby incorporated by reference in its entirety.

While the system 100 is illustrated with real-time imaging display at the remote image processing and display device 110, the ultrasound scanning device 130 may alone provide sufficient vascular navigations for locating a vessel of interest without any image display. Thus, the ultrasound scanning device 130 may be suitable for use in any situations without requiring an image processing and display system.

Figure 2A:
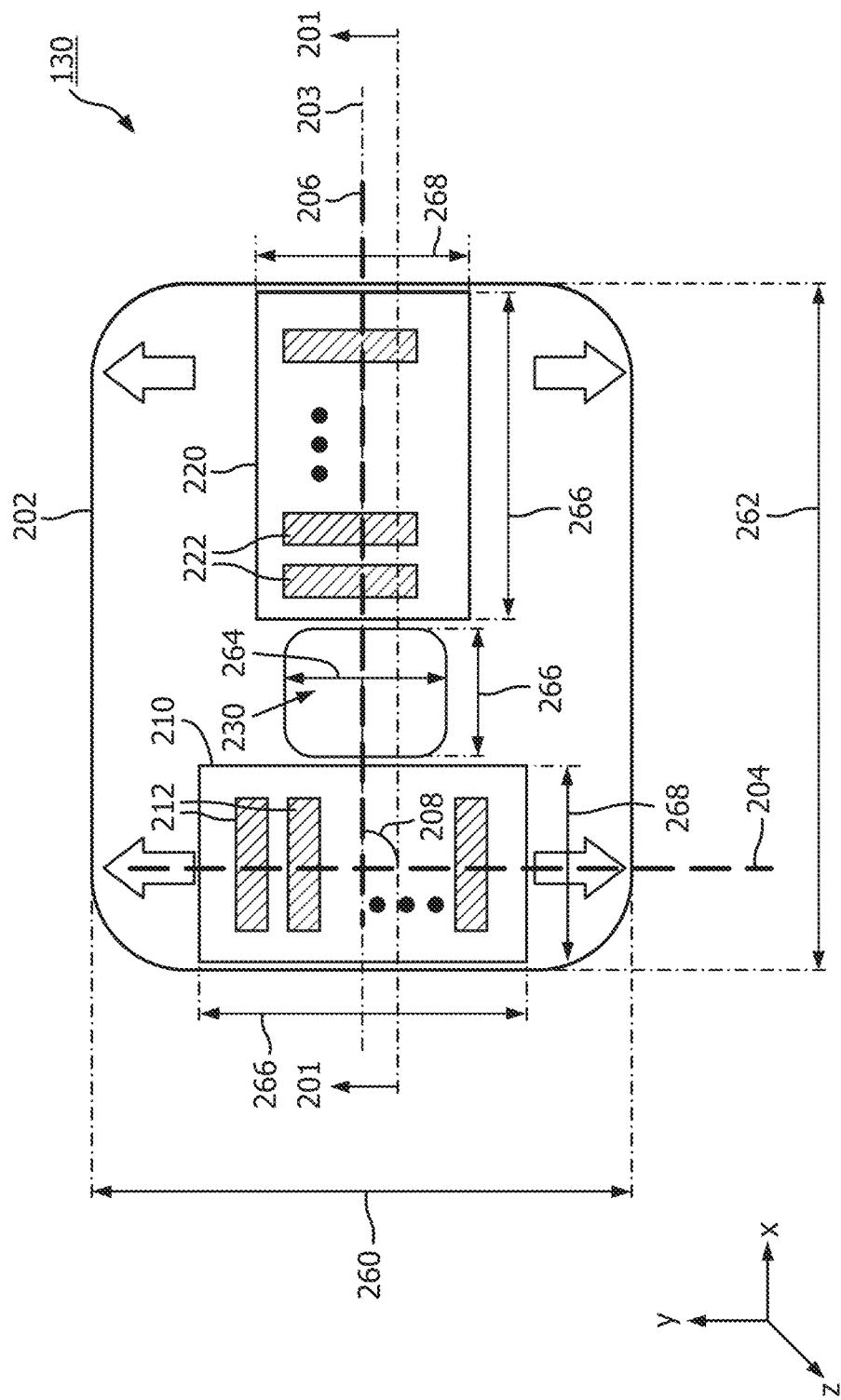
FIG. 2A is a schematic diagram illustrating a bottom view of an ultrasound scanning device, according to aspects of the present disclosure.
Figure 2B:
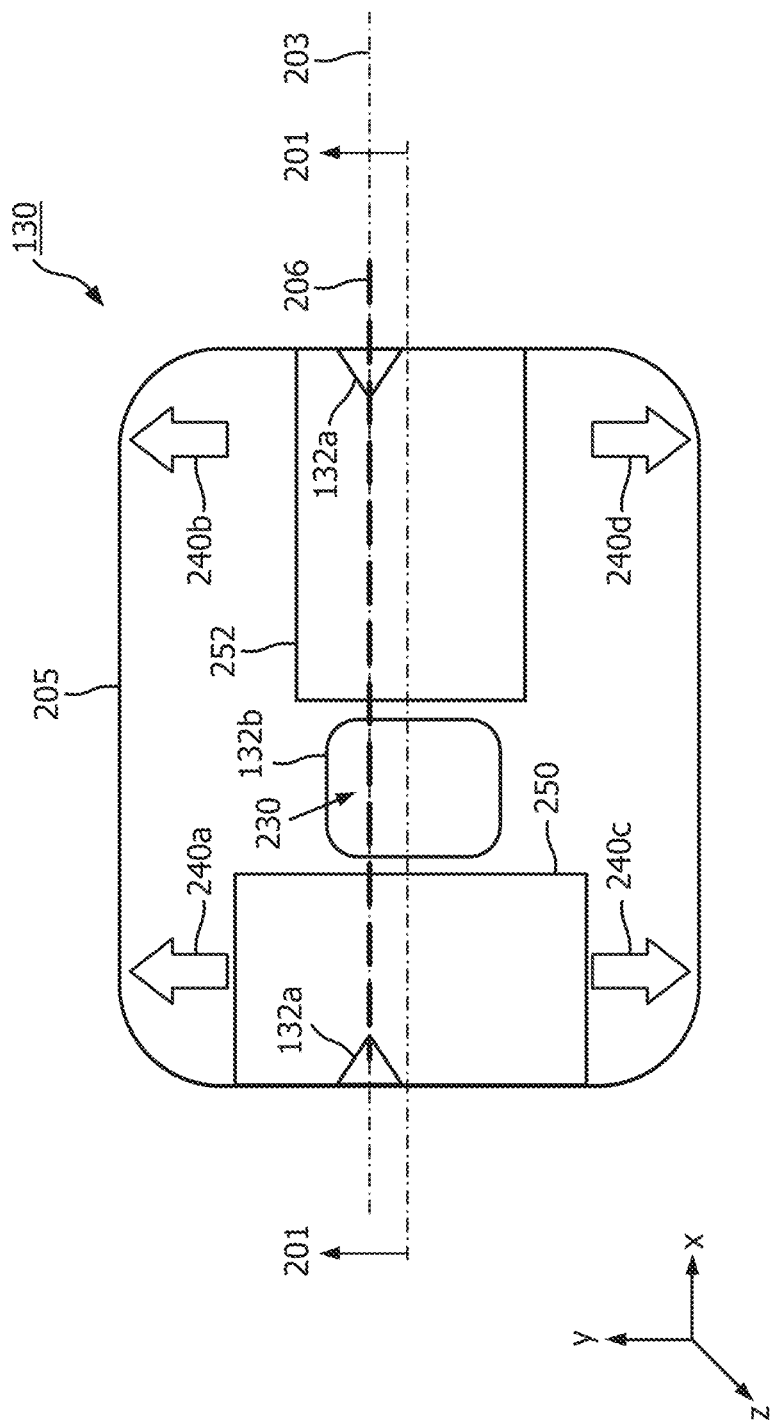
FIG. 2B is a schematic diagram illustrating a top view of an ultrasound scanning device, according to aspects of the present disclosure.
Figure 2C:
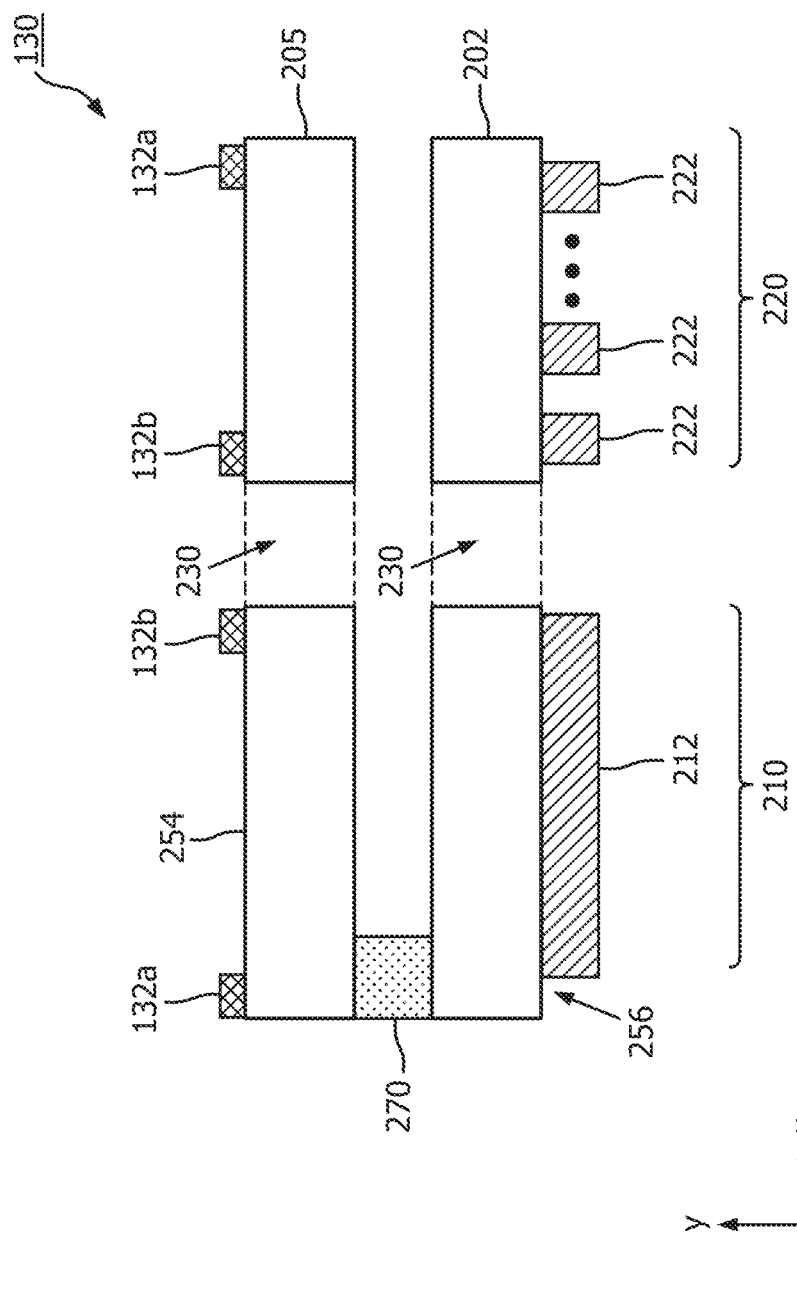
FIG. 2C is a schematic diagram illustrating a side view of an ultrasound scanning device, according to aspects of the present disclosure.

FIG. 2A is a schematic diagram illustrating a bottom view of the ultrasound scanning device 130, according to aspects of the present disclosure. FIG. 2B is a schematic diagram illustrating a top view of the ultrasound scanning device 130, according to aspects of the present disclosure. FIG. 2C is a schematic diagram illustrating a side view of the ultrasound scanning device 130 taken along the lines 201 of FIG. 2A and FIG. 2B, according to aspects of the present disclosure. The ultrasound scanning device 130 includes ultrasound components 210 and 220, visual directional indicators 240 (e.g., shown as 240a, 240b, 240c, and 240d), visual alignment indicators 132 (e.g., shown as 132a and 132b), and visual outline indicators 250 and 252. The ultrasound components 210 and 220 may be disposed on a backside or a bottom plane 256 (e.g., on an x-y plane) of a bottom circuit board 202 as shown in FIGS. 2A and 2C. The visual directional indicators 240, the visual alignment indicators 132, and the visual outline indicators 250 and 252 may be disposed on a top plane 254 (e.g., on an x-y plane) of a top circuit board 205 as shown in FIGS. 2B and 2C.

The top circuit board 205 may be stacked on top of the bottom circuit board 202 and housed in a rigid housing. In one embodiment, the top circuit board 205 and the bottom circuit board 202 are flexible printed circuit boards (PCBs). In another embodiment, the top circuit board 205 and the bottom circuit board 202 are rigid PCBs. In yet another embodiment, the top circuit board 205 is a rigid PCB and the bottom circuit board 202 is a flexible PCB. The top circuit board 205 and the bottom circuit board 202 may be interconnected by an inter-board connector 270 as shown in FIG. 2C. The inter-board connector 270 can include conductive wires interconnecting signal paths between the top circuit board 205 and the bottom circuit board 202. While the inter-board connector 270 are shown to interconnect the top circuit board 205 and the bottom circuit board 202 at the edges of the top circuit board 205 and the bottom circuit board 202, the inter-board connectors 270 may be positioned at any suitable location. The ultrasound scanning device 130 may include other components (e.g., a battery pack and a signal processing component), as described in greater detail herein.

The ultrasound component 210 includes a one-dimensional (1D) array of ultrasound transducer elements 212 positioned along an axis 204 (e.g., the y-axis) and spaced apart from each other. The ultrasound component 220 includes a 1D array of ultrasound transducer elements 222 positioned along an axis 206 (e.g., the x-axis) and spaced apart from each other. The axis 204 may be at an angle 208 with respect to the axis 206. In some embodiments, the axes 204 and 206 may be orthogonal to each other (e.g., the angle 208 is about 90 degrees).

The ultrasound component 210 may include about 128 ultrasound transducer elements 212 or any suitable number of ultrasound transducer elements 212 in the array. Similarly, the ultrasound component 220 may include about 128 ultrasound transducer elements 222 or any suitable number of ultrasound transducer elements 222 in the array. The ultrasound transducer elements 212 and 222 may be substantially similar. For example, the ultrasound transducer elements 212 and 222 may be piezoelectric zirconate transducer elements (PZT) transducer elements such as bulk PZT transducer elements, capacitive micromachined ultrasound transducer elements (cMUTs), single crystal piezoelectric materials, other suitable ultrasound transmitters and receivers, and/or combinations thereof. The ultrasound transducer elements 212 and 222 may generate ultrasonic waves at a frequency between about 4 megahertz (MHz) to about 15 MHz. The ultrasonic wave frequency may vary in different embodiments depending on the design of the ultrasound transducer elements 212 and 222 and/or the signal processing techniques applied by the ultrasound component 210. In some embodiments, when the ultrasound components 210 and 220 are cMUTs, the ultrasound components 210 and 220 can be integrated into a single device to provide bi-plane imaging functionalities.

The ultrasound scanning device 130 may be placed on a surface of a patient's anatomy (e.g., the arm 102), where the x-y plane (e.g., the backside of the ultrasound device 130) is adjacent to the patient's anatomy. The ultrasound transducer elements 212 may emit ultrasonic energy towards the patent's anatomy in a direction along the z-axis. The elementary pitch of the array of ultrasound transducer elements 212 may be constant and may be configured to provide a suitable lateral resolution along the axis 204. A set of one or more ultrasound transducer elements 212 may be triggered to transmit ultrasound signals and/or receive echo signals at a given time. The echo signals received from the set of ultrasound transducer elements 212 may create a scan line representative of the patient's anatomy. The ultrasound transducer elements 212 may be configured to create scan lines that progress along the axis 204. For example, the ultrasound component 210 may provide an image plane in a y-z plane.

The ultrasound transducer elements 222 may be substantially similar to the ultrasound transducer elements 212. Similar to the ultrasound transducer elements 212, the ultrasound transducer elements may 222 may emit ultrasonic energy along towards the patent's anatomy in a direction along the z-axis. The elementary pitch of the ultrasound transducer elements 222 may be constant and may be configured to provide a suitable lateral resolution along the axis 206. The ultrasound transducer elements 222 may be configured to create scan lines progressing along the axis 206. For example, the ultrasound component 220 may provide an image plane in an x-z plane. Thus, the ultrasound components 210 and 220 may provide images with orthogonal lateral resolutions or orthogonal image planes, which may be referred to as biplane imaging. The scan lines generated by the ultrasound components 210 and 220 may be referred to as bi-plane scan lines. For example, the ultrasound components 210 and 220 may be configured as described in U.S. Provisional Application No. 62/542,484, filed Aug. 8, 2017 and titled "ACTIVE SELECTABLE CMUT ULTRASOUND TRANSDUCER(S) IN A CMUT ARRAY CONFIGURATION" and U.S. Provisional Application. No. 62/569,839, filed Oct. 9, 2017 and titled "CAPACITIVE MICRO-MACHINED ULTRASOUND TRANSDUCER (CMUT) DEVICES AND CONTROL METHODS", which are hereby incorporated by reference in their entirety.

In an embodiment, the ultrasound scanning device 130 may include an alignment axis 203. The alignment axis 203 may be aligned to a central long axis (e.g., the axis 206 as shown) of the ultrasound component 220. The ultrasound scanning device 130 may process the echo data and may direct a clinician to orient the ultrasound scanning device 130 such that the alignment axis 203 of the ultrasound scanning device 130 is aligned with the axis of blood flow in the vessel, as described in greater detail herein. In some embodiments, the alignment axis 203 may have a fixed predetermined offset from the axis 204. In such embodiments, the ultrasound scanning device 130 may account for the offset when determining the orientation.

The ultrasound scanning device 130 may further include a processing component (e.g., a processing component 420 shown in FIG. 4) in communication with the ultrasound components 210 and 220 and the visual directional indicators 240. The processing component may receive echo (ultrasound) signals from the ultrasound components 210 and 220 and may determine an orientation of the ultrasound scanning device 130 (e.g., the alignment axis 203) with respect to a vessel of interest, for example, based on brightness-mode processing and/or Doppler processing as described in greater detail herein. The directional visual indicators 240 may include arrows indicating corresponding directions to move and/or rotate the ultrasound scanning device 130. The visual directional indicators 240 may be substantially similar to the visual alignment indicators 132. For example, the visual directional indicators 240 may include LEDs or any illuminable elements that can be activated and deactivated. The processing component may illuminate (e.g., activate) one or more of the visual directional indicators 240 to prompt a clinician to rotate and/or slide the ultrasound scanning device 130 into a final position, as described in greater detail herein. The visual alignment indicator 132b may be aligned to the axis 206.

The visual outline indicators 250 and 252 may include visible graphical lines marked on the top circuit board 205. The visual outline indicators 250 and 252 on the top circuit board 205 may be aligned with the perimeters or outer boundaries of the ultrasound component 210 and 220 on the bottom circuit board 202, respectively. Thus, the visual outline indicators 250 and 252 may indicate the positions of the ultrasound components 210 and 220, respectively, on the ultrasound scanning device 130. A clinician may determine whether to orient the ultrasound scanning device 130 for longitudinal imaging or transverse imaging based on the visual outline indicators 250 and 252.

In an embodiment, the ultrasound scanning device 130 may include an opening 230 positioned between the ultrasound components 210 and 220 such that the ultrasound components 210 and 220 are spaced apart from each other. The opening 230 may be rectangular in shape or any suitable shape. As shown in FIG. 2C, the opening 230 may extend through the ultrasound scanning device 130 from the top plane 254 of the top circuit board 205 of the ultrasound scanning device 130 to the bottom plane 256 of the bottom circuit board 202 of the ultrasound scanning device 130. The opening 230 may be positioned in alignment with the alignment axis 203. For example, the opening 230 may be centered at the alignment axis 203. The opening 230 may be configured to receive a medical device (e.g., the needle 140 or a catheter) for insertion into the vessel of interest after the ultrasound scanning device 130 is in alignment with the vessel of interest. In some embodiments, the opening 230 may be alternatively configured to position at a different location on the ultrasound scanning device 130 and the processing component may account for the location of the opening 230 when determining the orientation of the ultrasound scanning device 130.

Dimensions of the ultrasound scanning device 130 can vary in different embodiments. In some embodiments, the ultrasound components 210 and 220 each may have a length 266 of about 1.5 centimeter (cm) to about 3 cm and a width 268 of about 0.8 cm to about 1 cm. The ultrasound scanning device 130 may have a width 260 of about 4.5 cm and a length 262 of about 7 cm. The opening 230 may have a width 264 of about 1.25 cm and a length 266 of about 1.25 cm. Thus, the ultrasound scanning device 130 may have a compact form factor.

The use of the flexible PCBs for the bottom circuit board 202 and/or the top circuit board 205 may allow the ultrasound scanning device 130 to function as a flexible patch that can easily be placed on a patient's anatomy. While the ultrasound scanning device 130 can employ a matrix sensor array in place of the ultrasound components 210 and 220 with 1D ultrasound transducer arrays, the use of the 1D ultrasound transducer arrays may provide sufficient bi-plane imaging information at a lower cost and with a more compact form factor.

Figure 3:
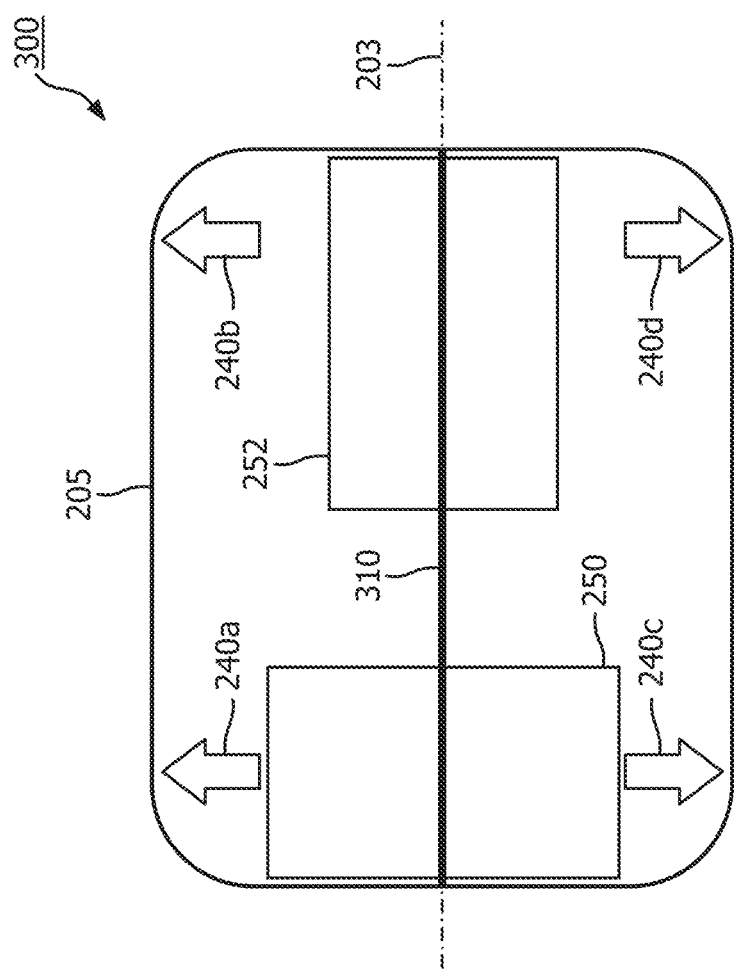
FIG. 3 is a schematic diagram illustrating a visual indicator configuration for an ultrasound scanning device, according to aspects of the present disclosure.

FIG. 3 is a schematic diagram illustrating a visual indicator configuration 300 for the ultrasound scanning device 130, according to aspects of the present disclosure. FIG. 3 illustrates an alternative configuration 300 for the top circuit board 205. In the configuration 300, the opening 230 is absent in the top circuit board 205. For example, when the ultrasound scanning device 130 employs the configuration 300 for the top circuit board 205, a clinician may insert a needle (e.g., the needle 140) at the edge of the ultrasound scanning device 130, for example, as marked by the visual alignment indicators 132a, instead of through the opening 230 as described above with respect to FIGS. 2A-2C. In addition, the top circuit board 205 may include a visual alignment indicator 310 aligned with the alignment axis 203. The visual alignment indicator 310 may be a graphical line and/or illuminated when in alignment. A clinician may insert a needle at the edge of the ultrasound scanning device following the visual alignment indicator 310, as described in greater detail herein. When the ultrasound scanning device 130 uses the configuration 300 for the top circuit board 205, the bottom circuit board 202 may also exclude the opening 230.

Figure 4:
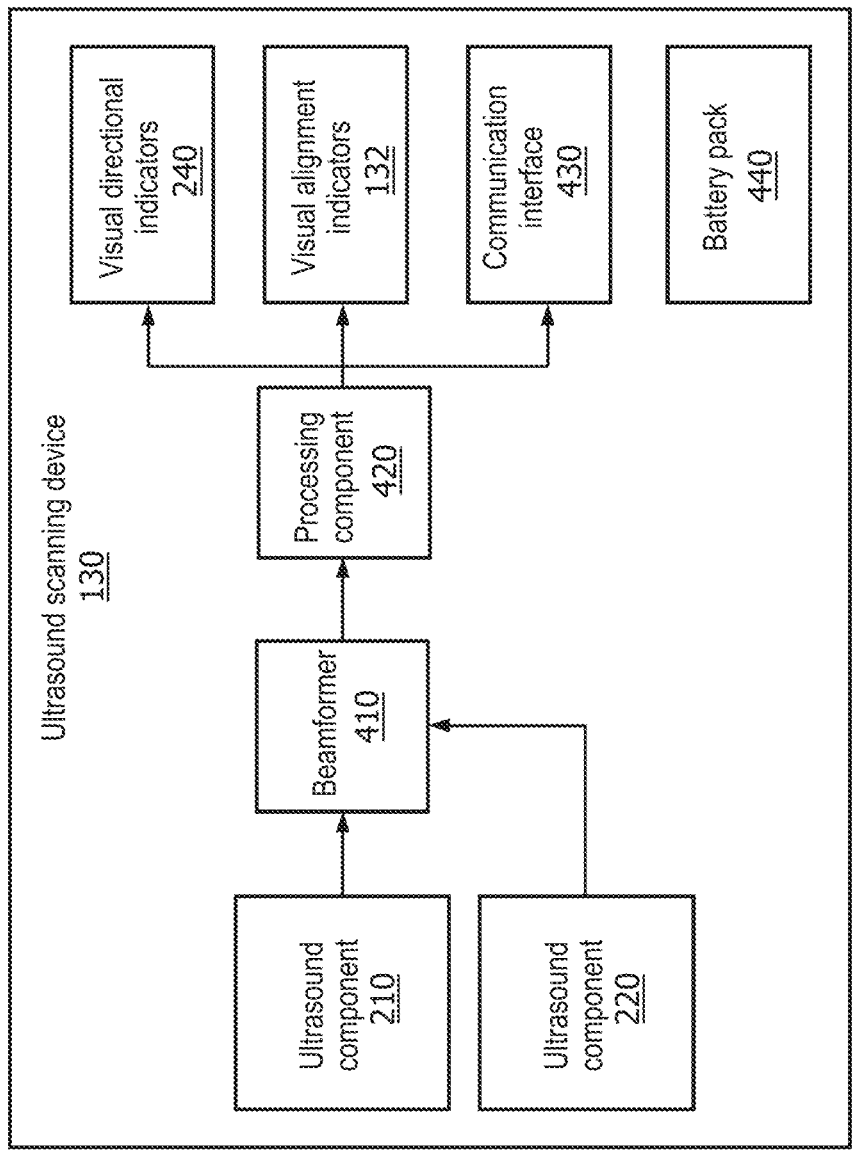
FIG. 4 is a schematic diagram illustrating internal components of an ultrasound scanning device, according to aspects of the present disclosure.

FIG. 4 is a schematic diagram illustrating internal components of the ultrasound scanning device 130, according to aspects of the present disclosure. The ultrasound scanning device 130 includes the ultrasound components 210 and 220, a beamformer 410, a processing component 420, the visual directional indicators 240, the visual alignment indicators 132, and a communication interface 430. For instance, the beamformer 410 may be disposed on the bottom circuit board 202 in addition to the ultrasound components 210 and 220 and the processing component 420 and the communication interface 430 may be disposed on the top circuit board 205 in addition to the visual directional indicators 240 and the visual alignment indicators 132.

The beamformer 410 is coupled to the ultrasound components 210 and 220. The beamformer 410 may include a main beamformer and/or multiple stages of micro-beamformers, for example, including signal add elements, signal delay elements, phase control elements, and/or circuit logics. The beamformer 410 can be configured to control the operations of the array of ultrasound transducer elements 212 in the ultrasound component 210 and the array of ultrasound transducer elements 222 in the ultrasound component 220. The beamformer 410 can trigger one or more of the ultrasound transducer elements 212 to transmit ultrasound signals and/or receive echo signals to create a scan line (e.g., in the y-z plane of FIG. 3). Similarly, the beamformer 410 can trigger one or more of the ultrasound transducer elements 222 to transmit ultrasound signals and/ or receive echo signals to create a scan line (e.g., in the x-z plane of FIG. 3).

The beamformer 410 can configure the array of ultrasound transducer elements 212 or 222 to function as a linear sequential array or as a phased-array where the acoustic beams emanate from a single point on the transducer array. For example, the beamformer 410 can control the time-delay and/or the phase of an ultrasound signal transmission and/or an echo response reception at each ultrasound transducer element 212 or 222. The beamformer 410 can configure the ultrasound components 210 and 220 to produce a linear pattern of scan lines. The outer boundaries of the scan lines may form a rectangular-shaped, a parallelogram-shaped, or a fan-shaped pattern of scan lines. In the case of a fan-shaped pattern, the outer boundaries form a sector shape. Other variations of scan line patterns may be utilized, as is well known in the art. For each of the ultrasound components 210 and 220, the scan line patterns generated therefrom are co-planar since the elements themselves are preferably co-linear within the component. The beamformer 410 can configure the ultrasound components 210 and 220 such that scan lines from the ultrasound component 210 may intersect with scan lines from the ultrasound component 220. The processing component 420 is coupled to the beamformer 410 and/or the ultrasound components 210 and 220. The processing component 420 may include field-programmable gate array (FPGA), micro-controllers, and/or other circuit logics configured to apply various signal processing techniques to the beamformed signals output by the beamformer 410. Some examples of signal processing may include in-phase, quadrature-phase (IQ) computation, magnitude calculation, compression, filtering, flow processing, Doppler processing, and/or image-mode processing.

In an embodiment, the processing component 420 may determine gray-scale measures (e.g., signal intensity measures) from the received echo signals. For example, the processing component 420 may represent the amplitudes of the echo signals by intensity levels.

In an embodiment, the processing component 420 may perform Doppler processing based on the received echo signals. For example, the beamformer 410 may configure the ultrasound transducer elements 212 to emit ultrasound waves at an angle with respect to a vessel of interest. The ultrasound waves may be backscattered by the moving blood flow travelling at a particular velocity and a particular direction in the vessel. The backscattered ultrasound waves are received by the ultrasound transducer elements 212. The frequencies of the received backscattered ultrasound waves are Doppler-shifted by an amount proportional to the blood flow velocity. Thus, the processing component 420 can analyze the echo data to characterize the blood flow (e.g., to determine an axis of blood flow) in the vessel and determine an orientation of the ultrasound scanning device 130 with respect to the vessel based on the blood flow characterization. Doppler ultrasound measures the movement of objects through the emitted beam as a phase change in the received signal. When ultrasound waves are reflected from a moving structure (e.g., a red blood cell within the vessel), the wavelength and the frequency of the returning waves are shifted. If the moving structure is moving toward the transducer, the frequency increases. If the moving structure is moving away from the transducer, the frequency decreases.

In an embodiment, the processing component 420 can employ the Doppler Equation:

$$\Delta f = (2 \times f0 \times V \times \cos \theta)/C \qquad (1)$$

where $\Delta f$ is the frequency shift, $f\theta$ is the frequency of the transmitted wave, V is the velocity of the reflecting object (e.g., a red blood cell), $\theta$ is the angle between the incident wave and the direction of the movement of the reflecting object (i.e., the angle of incidence), and C is the velocity of sound in the medium. The frequency shift is maximal when the transducer is oriented parallel to the direction of the blood flow and the $\theta$ is zero degrees ($\cos 0=1$). The frequency shift is absent when the transducer is oriented perpendicular to the direction of the blood flow and the $\theta$ is 90 degrees ($\cos 90=0$). Higher Doppler frequency shifts are obtained when the velocity is increased, the incident wave is more aligned with the direction of blood flow, and/or when a higher frequency is emitted.

Figure 6B:
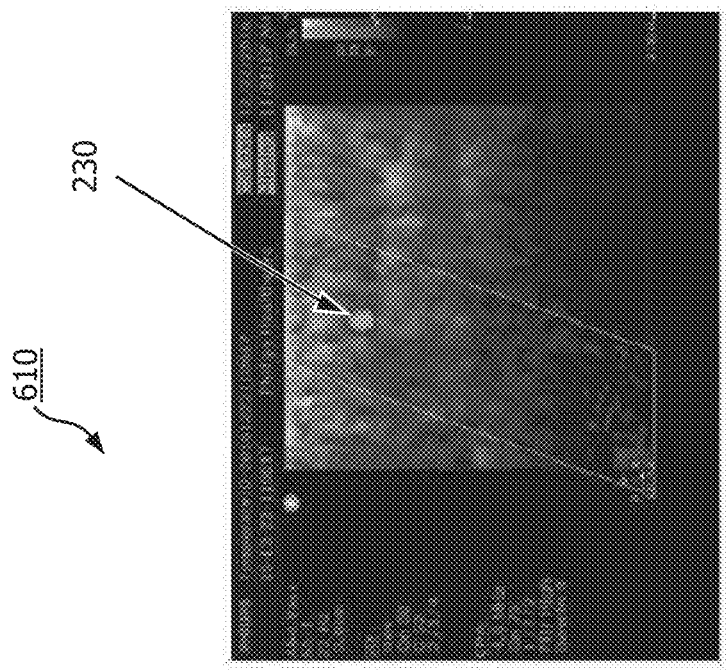
FIG. 6B is a color flow image of a lateral view of a vessel, according to aspects of the present disclosure.
Figure 6A:
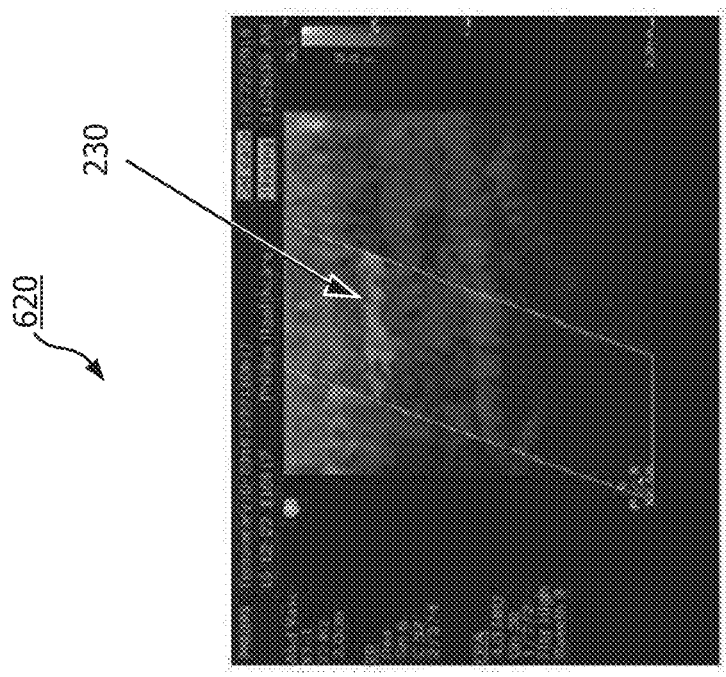
FIG. 6A is a color flow image of a transverse view of a vessel, according to aspects of the present disclosure.

The processing component 420 may apply similar gray-scale processing and/or Doppler processing to the echo responses received from ultrasound transducer elements 222 of the ultrasound component 220. For example, depending on the orientation of the ultrasound scanning device 130, the gray-scale measures obtained from the ultrasound component 210 may provide a transverse view of the vessel and the Doppler measures obtained from the ultrasound component 210 may detect a blood flow in the vessel. With the same orientation, the gray-scale measures obtained from the ultrasound component 220 may provide a lateral view of the vessel, where the blood flow may be shown as an elongated anechoic region, and the Doppler measures obtained from the ultrasound component 220 may detect turbulences of blood flow in the vessel. FIGS. 6A and 6B provide examples of color flow images in a transverse vessel view and in a lateral vessel view.

The visual directional indicators 240 and the visual alignment indicators 132 are coupled to the processing component 420. After determining an orientation of the ultrasound scanning device 130 with respect to the vessel, the processing component 420 may determine a direction or a position to move and/or rotate the ultrasound scanning device 130 so that the ultrasound scanning device 130 may be aligned with the vessel. The processing component 420 may indicate a direction and/or a position to move the ultrasound scanning device 130 by illuminating corresponding visual directional indicators 240. After the ultrasound scanning device 130 is aligned with the vessel, the processing component 420 may indicate the completion of the alignment and/or a needle insertion location by illuminating the visual alignment indicators 132.

The communication interface 430 is coupled to the processing component 420. The communication interface 430 may include hardware and/or software components configured to communicate with the remote image processing and display device 110 via the communication link 120. For example, the communication interface 430 may include a wireless communication device (e.g., an on-board Bluetooth® radio). The communication interface 430 may transmit digitized samples of echo signals, beamformed signals, processed image signals, and/or needle location information to the remote image processing and display device 110 for process and/or real-time display. The communication interface 430 may receive controls from the remote image processing and display device 110 for controlling the operations of the ultrasound scanning device 130.

In some embodiments, the ultrasound scanning device 130 may further include a rechargeable battery pack 440. The battery pack 440 may be disposed between the top circuit board 205 and the bottom circuit board 202 avoiding blockage to the central opening 230 when the ultrasound scanning device 130 includes the central opening 230. In some embodiments, the battery pack 440 may include two sub-packs, each disposed on either side of the central opening 230 between the top circuit board 202 and the bottom circuit board 205. The battery pack 440 may include an electrical energy storage that powers the components of the ultrasound scanning device 130, for example, including the ultrasound components 210 and 220, the beamformer 410, the processing component 420, the visual directional indicators 240, the visual alignment indicators 132, the communication interface 430, and/or any internal active components. In an embodiment, the battery pack 440 may include an electrical storage capacity sufficient to power the ultrasound scanning device for several hours.

Figure 5A:
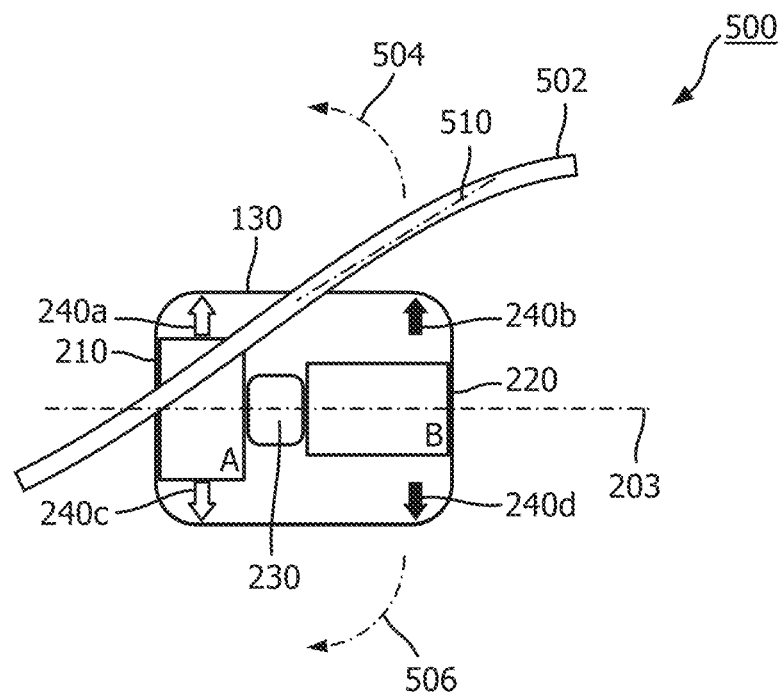
FIG. 5A illustrates positioning of an ultrasound scanning device during an initial stage of scanning, according to aspects of the present disclosure.

FIGS. 5A to 5D illustrate a use case scenario 500 for the ultrasound scanning device 130. In the scenario 500, a clinician may use the ultrasound scanning device 130 to locate a vessel for an intravenous access procedure. FIG. 5A illustrates positioning of the ultrasound scanning device 130 during an initial stage of scanning, according to aspects of the present disclosure. The clinician may begin an intravenous access procedure by identifying an approximate puncture site on a patient, for example, near a blood vessel 502. After identifying the approximate puncture site, the clinician may place the ultrasound scanning device 130 at the approximate site. The placement of the ultrasound scanning device 130 at the approximate site may allow at least one of the ultrasound components 210 and 220 to partially detect the vessel 502. The clinician may select to begin the placement for longitudinal or transversal guidance. For example, the clinician may begin with the placement for longitudinal guidance. As shown, the ultrasound component 210 may detect the blood vessel 502, whereas the ultrasound component 220 may not detect the blood vessel 502.

Figure 5B:
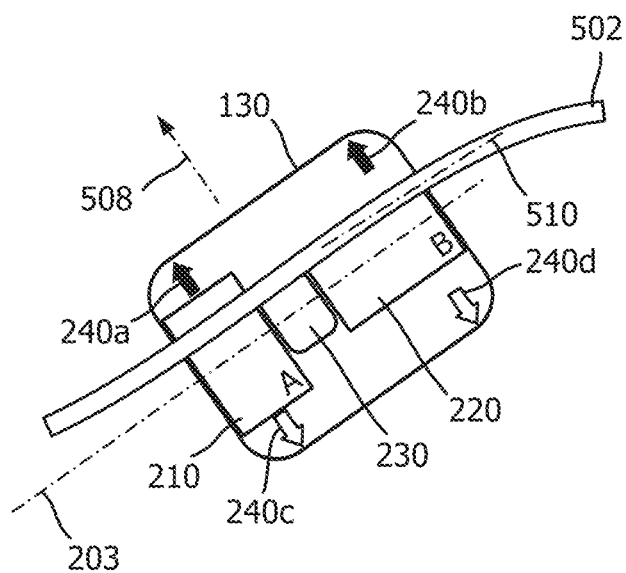
FIG. 5B illustrates positioning of an ultrasound scanning device during a refinement stage of scanning, according to aspects of the present disclosure.

With the placement as shown, the ultrasound scanning device 130 may determine that a rotation of the ultrasound scanning device 130 in a counter-clockwise direction 504 or a clockwise direction 506 may be required to align the alignment axis 203 with the blood vessel 502 (e.g., the axis 510 of blood flow). Thus, the ultrasound scanning device 130 may illuminate the visual directional indicators 240b and 240d (e.g., with red light or any color light) to direct the clinician to rotate the ultrasound scanning device 130. FIG. 5B illustrates positioning of the ultrasound scanning device 130 during a refinement stage of scanning, according to aspects of the present disclosure. For example, the clinician rotates the ultrasound scanning device 130 in the direction 504 based on the illuminated visual directional indicators 240b and 240d in the initial stage. After the rotation, both the ultrasound components 210 and 220 may detect the blood vessel 502. However, the detected signal from ultrasound component 220 may be weak since the blood vessel 502 may not be aligned with the center of the ultrasound component 220 (e.g., the ultrasound transducer elements 222). Thus, the ultrasound scanning device 130 may determine that a translation of the ultrasound scanning device 130 in a direction 508 may be required to align the alignment axis 203 with the blood flow axis 510. Thus, the ultrasound scanning device 130 may illuminate the visual directional indicators 240a and 240b (e.g., with red light or any color light) to direct the clinician to move the ultrasound scanning device 130 in the direction 508. In an embodiment, after the initial stage, the clinician may rotate the ultrasound scanning device 130 counter-clockwise in the direction 504 and/or clockwise in the direction 506 until the visual directional indicators 240a and 240b are illuminated (e.g., indicating an upward or left translation) or until the visual directional indicators 240c and 240d are illuminated (e.g., indicating a downward or right translation).

Figure 5C:
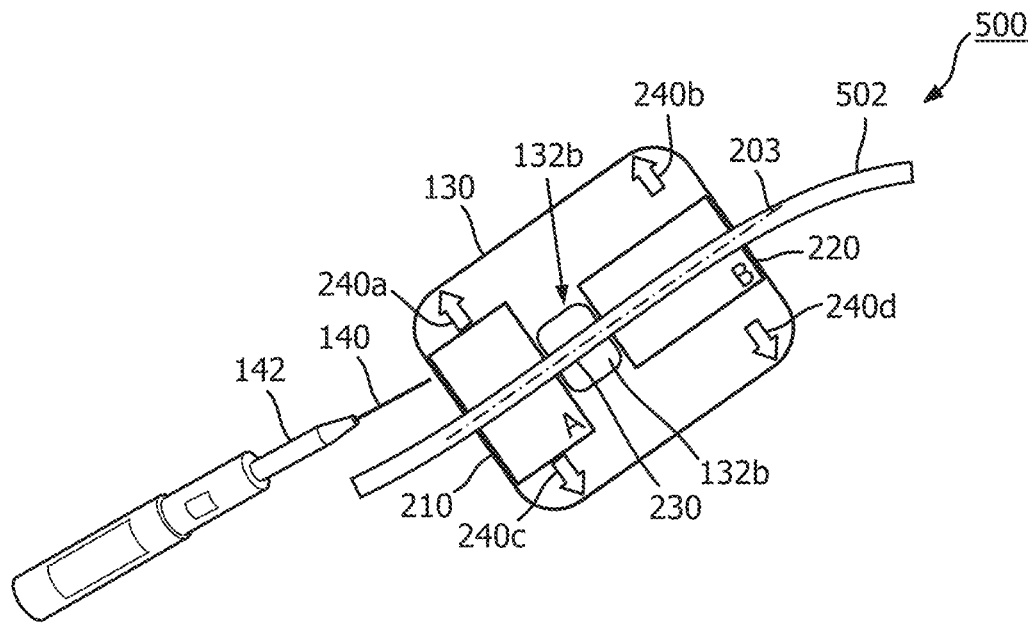
FIG. 5C illustrates an ultrasound scanning device in alignment with a vessel during a stage of scanning, according to aspects of the present disclosure.

FIG. 5C illustrates the ultrasound scanning device 130 in alignment with the vessel 502 during a stage of scanning, according to aspects of the present disclosure. For example, the clinician moved the ultrasound scanning device 130 in the direction 508 based on the illuminated visual directional indicators 240a and 240b in the refinement stage. The clinician may slide the ultrasound scanning device 130 in the direction 508 until the visual alignment indicator 132b is illuminated indicating that both the ultrasound components 210 and 220 can detect the presence of the vessel 502 and the alignment axis 203 is aligned with the vessel 502. When the alignment indicator 132b is illuminated (e.g., with green light or any colored light), the clinician may accurately insert the needle 140 through the opening 230 to reach the vessel 502. For example, the needle 140 may be coupled to a hub 142. After the clinician inserted the needle 140 into the vessel 502, the clinician may remove the needle 140 leaving the hub 142 in place on the patient. Subsequently, the clinician may remove the ultrasound scanning device 130 by allowing the hub 142 to pass through the opening 230.

Figure 5D:
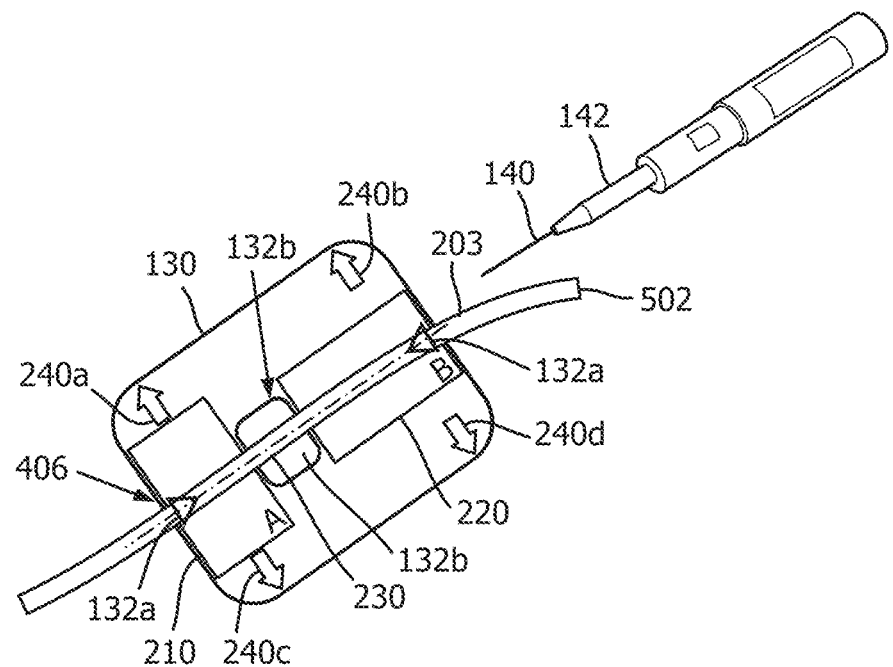
FIG. 5D illustrates an ultrasound scanning device in alignment with a vessel during a stage of scanning, according to aspects of the present disclosure.

FIG. 5D illustrates the ultrasound scanning device 130 in alignment with the vessel 502 during a stage of scanning, according to aspects of the present disclosure. FIG. 5D illustrates a substantially similar setting or scenarios as FIG. 5C. In the setting of FIG. 5D, the ultrasound scanning device 130 includes the illumination of the visual alignment indicators 132a at the edges of the ultrasound scanning device 130 in addition to the visual alignment indicator 132b. For example, the clinician may choose to insert the needle 140 at the edge of the ultrasound scanning device 130 as indicated by the visual alignment indicator 132a and/or 310 to reach the vessel 502. FIG. 6A is a color flow image 610 of a transverse view of the vessel 502, according to aspects of the present disclosure. For example, the image 610 shows Doppler measures or Doppler lines obtained from the ultrasound component 210 when the ultrasound scanning device 130 is aligned with the vessel 502, for example, as shown in FIGS. 5C and 5D. Since the linear progression of scan lines of the ultrasound component 210 is orthogonal to the vessel 502, only a subset of the scan lines (e.g., located at about the center of the scan line pattern) may cross the vessel 502 and may detect Doppler shifts from the blood flow in the vessel 502. Thus as shown in FIG. 6A, the Doppler measures or Doppler lines from the ultrasound component 210 may detect Doppler-shifts as seen by the blood flow shown in the region 612. Because the direction of blood flow is transverse, not in the direction of echo propagation along the individual scan lines crossing region 612, the Doppler-shifts detected may be due to turbulent movement of reflectors in the blood flow.

FIG. 6B is a color flow image 620 of a lateral view of the vessel 502, according to aspects of the present disclosure. For example, the image 620 shows Doppler measures or Doppler lines obtained from the ultrasound component 220 when the ultrasound scanning device 130 is aligned with the vessel 502, for example, as shown in FIGS. 5C and 5D. Since the linear progression of scan lines of the ultrasound component 210 is parallel to or aligned with the vessel 502, most or all of the scan lines may cross the region of blood flow shown in the region 622. Because the scan lines are also angled with respect to the direction of flow, that is, the line pattern forms a parallelogram, the Doppler measures or Doppler lines of the ultrasound component 220 may detect Doppler-shifts as displacements of blood reflectors in flow through the vessel. Thus, the processing component 420 can analyze Doppler measures obtained from the ultrasound components 210 and 220 to determine an orientation of the ultrasound scanning device 130 with respect to the vessel 502 based on the amount of Doppler-shifts detected, the position of the detected flow regions 612 and 622, and the extent of the regions across the scan line patterns.

Figure 7:
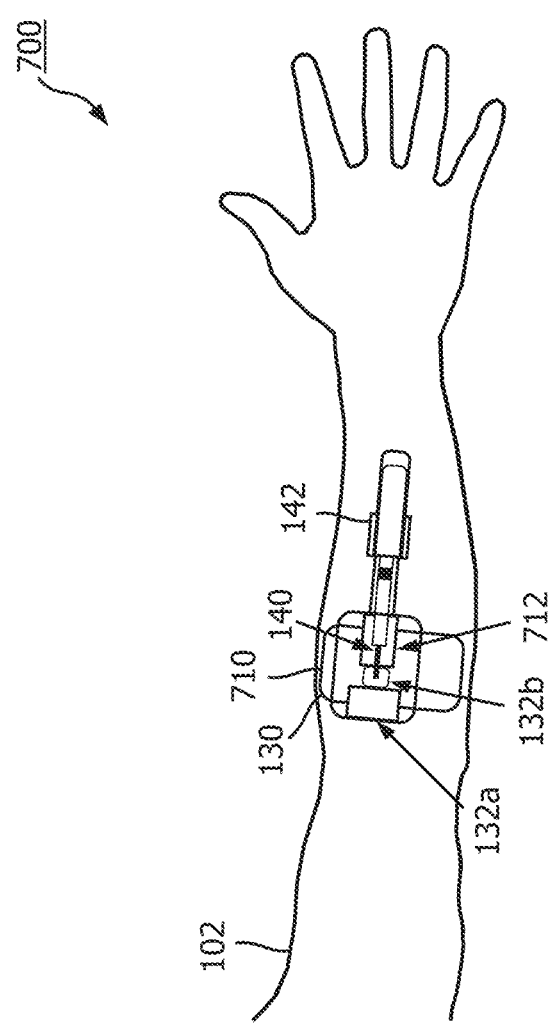
FIG. 7 illustrates a use case scenario for an ultrasound scanning device, according to aspects of the present disclosure.

FIG. 7 illustrates a user case scenario 700 for the ultrasound scanning device 130, according to aspects of the present disclosure. For example, a clinician may have aligned the ultrasound scanning device 130 to a vessel (e.g., the vessel 502) in the patient's arm 102 using mechanisms as described above in the scenario 500 with respect to FIGS. 5A to 5D. In the scenario 700, after the alignment is completed, the clinician may affix the ultrasound scanning device 130 to the patient's arm using a clear (e.g., transparent) sterile adhesive band 710 before inserting the needle 140 into the vessel. The adhesive band 710 may include an opening 712 aligned with the opening 230 of the ultrasound scanning device 130. The adhesive band 710 may only cover portions of the ultrasound scanning device 130 exposing the edges of the ultrasound scanning device 130. Thus, the clinician may choose to insert the needle 140 into the vessel through the opening 230 as shown or at the edge where the visual alignment indicator 132a is lit up. After the insertion is completed, the clinician may remove the adhesive band 710 and the ultrasound scanning device 130. The application of the adhesive band 710 may secure the ultrasound scanning device 130 during the insertion, freeing the clinician to focus on the insertion instead of holding the ultrasound scanning device on the patient by hand.

Figure 8:
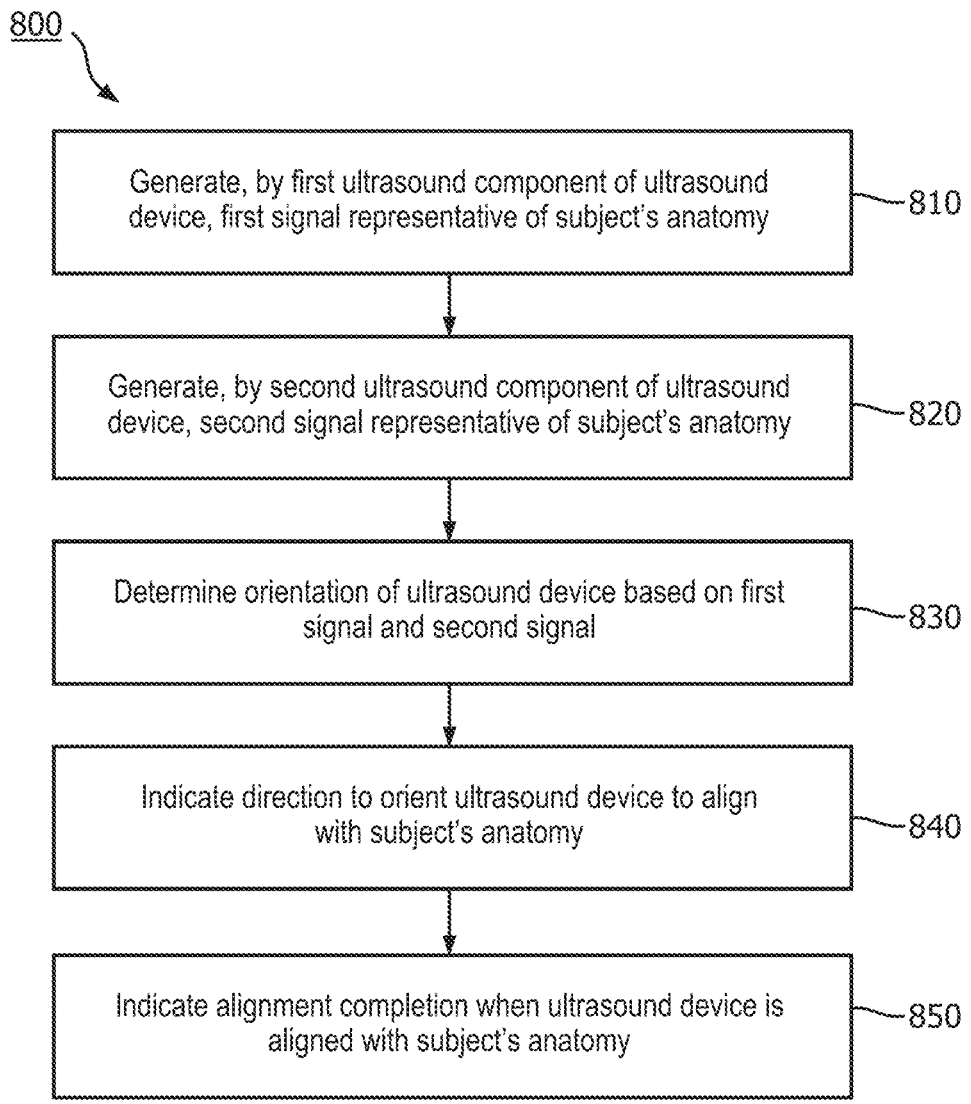
FIG. 8 is a flow diagram of a method of ultrasound scanning, according to aspects of the disclosure.

FIG. 8 is a flow diagram of a method 800 of ultrasound scanning for vascular navigation, according to aspects of the disclosure. Steps of the method 800 can be executed by the system 100. The method 800 may employ similar mechanisms as in the scenarios 500 and 700 as described with respect to FIGS. 4 and 7, respectively. As illustrated, the method 800 includes a number of enumerated steps, but embodiments of the method 800 may include additional steps before, after, and in between the enumerated steps. In some embodiments, one or more of the enumerated steps may be omitted or performed in a different order.

At step 810, the method 800 includes generating, by a first ultrasound component (e.g., the ultrasound component 210) of an ultrasound device (e.g., the ultrasound scanning device 130), a first signal representative of a subject's anatomy along a first axis. The subject's anatomy may be a patient's arm (e.g., the arm), leg, back, or any body parts. The first axis may correspond to the axis 204. The first signal may include scan lines generated by the first ultrasound component. In an embodiment, the first signal may be generated by beamforming a plurality of ultrasound echo signals received from an array of ultrasound transducers (e.g., the ultrasound transducer elements 212) of the first ultrasound component.

At step 820, the method 800 includes generating, by a second ultrasound component (e.g., the ultrasound component 220) of the ultrasound device, a second signal representative of the subject's anatomy along a second axis. The first axis disposed at an angle with respect to the second axis. The second axis may correspond to the axis 206. The angle may correspond to the angle 208. The second signal may include scan lines generated by the second ultrasound component. In an embodiment, the second signal may be generated by beamforming a plurality of ultrasound echo signals received from an array of ultrasound transducers (e.g., the ultrasound transducer elements 222) of the first ultrasound component. At step 830, the method 800 includes determining an orientation of the ultrasound device with respect to the subject's anatomy based on the first signal and the second signal. In an embodiment, the orientation may be determined based on signal intensity measures obtained from the first signal and the second signal. In an embodiment, the orientation may be determined based on Doppler measures obtained from the first signal and the second signal, for example, by applying Equation (1).

At step 840, the method 800 includes indicating a direction (e.g., the directions 504, 506, and 508) to orient the ultrasound device to align with the subject's anatomy, for example, based on the determined orientation. The indication may include illuminating visual directional indicators (e.g., the indicators 240), for example, as shown in FIGS. 5A and 5B. The direction may guide a clinician to align an axis (e.g., the alignment axis 203) of the ultrasound device with the subject's anatomy. For example, the subject's anatomy may include a blood vessel (e.g., the vessel 502) and the direction may guide the alignment of the ultrasound device with an axis (e.g., the axis 510) of blood flow in the vessel. In some embodiments, the first and second ultrasound components may each generate a separate image display, for example, showing the subject's body anatomy and/or the device orientation.

At step 850, the method 800 includes indicating an alignment completion when the ultrasound device is aligned with the subject's anatomy. The indicating may include illuminating visual alignment indicators (e.g., the indicators 132 and 310), for example, as shown in FIGS. 5C and 5D. Subsequently, the clinician may insert a medical device (e.g., the needle 140) into the blood vessel. For example, the clinician may insert the medical device through an opening (e.g., the opening 230) located between the first and second ultrasound components. Alternatively, the clinician may insert the medical device at an edge of the ultrasound device following an alignment line indicator (e.g., the alignment indicator 310).

Aspects of the present disclosure can provide several benefits. For example, the integration of the ultrasound components 210 and 220, the processing component 420, and the indicators 132 and 240 at the ultrasound scanning device 130 can guide a clinician in locating a vessel for a venipuncture without additional real-time imaging display. The configuration of the ultrasound components 210 and 220 to be oriented at an angle with respect to each other allows for the use of low-cost 1D transducer arrays to produce high-quality bi-plane images, that would be otherwise expensive requiring a high-cost matrix array or compromising image quality with a low-cost sparse matrix array. The use of the adhesive band 710 to secure the ultrasound scanning device 130 after the alignment can avoid shifting the ultrasound scanning device 130 during the insertion and allows a clinician with hands-free operations (e.g., no hand holding of the ultrasound scanning device 130) during the insertion. The ultrasound scanning device 130 may be suitable for use under any settings including emergency settings. The ultrasound scanning device 130 can allow a clinician to focus on the venipuncture instead of finding a suitable vessel. Thus, the ultrasound scanning device 130 can improve efficiency, accuracy, and safety for intravenous access procedures. The disclosed embodiments are suitable for use in guiding clinicians to locate a blood vessel in any body part. The disclosed embodiments may additionally facilitate real-time imaging for needle tracking.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An ultrasound device, comprising:
   a housing; and
   at least one circuit board disposed within the housing, wherein the at least one circuit board comprises:
   a first ultrasound transducer array arranged along a first axis of the ultrasound device and configured to generate a first ultrasound signal representative of a subject's anatomy along the first axis;
   a second ultrasound transducer array arranged along a second axis of the ultrasound device and configured to generate a second ultrasound signal representative of the subject's anatomy along the second axis, the first axis disposed at an angle with respect to the second axis;
   a plurality of directional indicators respectively pointing outward from the housing, wherein the plurality of directional indicators are disposed at a plurality of corresponding locations of the housing such that the plurality of directional indicators are spaced from one another; and a logic circuit in communication with the first ultrasound transducer array, the second ultrasound transducer array, and the plurality of directional indicators,
wherein the logic circuit is configured to:
determine an orientation of the ultrasound device with respect to the subject's anatomy based on the first ultrasound signal and the second ultrasound signal;
determine if the first axis is unaligned with the subject's anatomy based on the orientation; and
activate, when the first axis is unaligned with the subject's anatomy, a directional indicator of the plurality of directional indicators based on the determined orientation such that the directional indicator that is activated is configured to provide an indication to a user to move a corresponding location of the housing in a direction that the directional indicator points to align the first axis with the subject's anatomy,
wherein the at least one circuit board comprises a first circuit board and a second circuit board parallel to the first circuit board,
wherein the first ultrasound transducer array and the second ultrasound transducer array are disposed on the first circuit board in an orientation facing the subject's anatomy,
wherein the plurality of directional indicators are disposed on the second circuit board in an orientation facing the user, and
wherein the plurality of directional indicators includes light emitting diodes (LEDs).

2. The ultrasound device of claim 1, wherein the first axis is orthogonal to the second axis.

3. The ultrasound device of claim 1, wherein the logic circuit is further configured to:
determine Doppler measures based on the first ultrasound signal and the second ultrasound signal; and
determine the orientation based on the Doppler measures.

4. The ultrasound device of claim 1, wherein the logic circuit is further configured to:
determine signal intensity measures based on the first ultrasound signal and second ultrasound signal; and
determine the orientation based on the signal intensity measures.

5. The ultrasound device of claim 1, wherein the plurality of directional indicators comprise an arrow.

6. The ultrasound device of claim 1,
wherein the at least one circuit board comprises one or more alignment indicators different than the plurality of directional indicators,
wherein the subject's anatomy includes a blood vessel, and
wherein the logic circuit is further configured to:
determine that the first axis of the ultrasound device is aligned with an axis of blood flow in the blood vessel; and
indicate, via the one or more alignment indicators, an alignment completion in response to determining that the first axis of the ultrasound device is aligned with the axis of blood flow in the blood vessel.

7. The ultrasound device of claim 6, wherein the one or more alignment indicators comprises at least one of a light, a triangular shape, or a graphical line.

8. The ultrasound device of claim 1, further comprising:
a top plane;
a bottom plane opposite the top plane; and
an opening extending through the ultrasound device from the top plane to the bottom plane, the opening aligned with the first axis of the ultrasound device and configured to receive a medical device for insertion into the blood vessel, wherein the medical device comprises at least one of a needle or a catheter.

9. The ultrasound device of claim 8, wherein the first ultrasound transducer array and the second ultrasound transducer array are spatially separated by the opening.

10. The ultrasound device of claim 1, further comprising a communication interface in communication with the logic circuit and a remote device, the communication interface configured to transmit the first ultrasound signal and the second ultrasound signal to the remote device for displaying an image of the subject's anatomy based on at least one of the first ultrasound signal or the second ultrasound signal.

11. The ultrasound device of claim 10, wherein the logic circuit is further configured to receive, via the communication interface, a control signal for configuring at least one of the first ultrasound transducer array or the second ultrasound transducer array.

12. The ultrasound device of claim 10, wherein the communication interface is a wireless link.

13. A method of ultrasound scanning, comprising:
generating a first ultrasound signal by a first ultrasound transducer array of an ultrasound device, wherein the ultrasound device comprises:
a housing; and
at least one circuit board disposed within the housing, wherein the at least one circuit board comprises:
the first ultrasound transducer array arranged along a first axis of the ultrasound device, wherein the first ultrasound signal is representative of a subject's anatomy along the first axis of the ultrasound device;
a second ultrasound transducer array arranged along a second axis of the ultrasound device, wherein the first axis is disposed at angle with respect to the second axis;
a plurality of directional indicators respectively pointing outward from the housing, wherein the plurality of directional indicators are disposed at a plurality of corresponding locations of the housing such that the plurality of directional indicators are spaced from one another; and
a logic circuit in communication with the first ultrasound transducer array, the second ultrasound transducer array, and the plurality of directional indicators,
wherein the at least one circuit board comprises a first circuit board and a second circuit board parallel to the first circuit board,
wherein the first ultrasound transducer array and the second ultrasound transducer array are disposed on the first circuit board in an orientation facing the subject's anatomy,
wherein the plurality of directional indicators are disposed on the second circuit board in an orientation facing the user, and
wherein the plurality of directional indicators includes light emitting diodes (LEDs),
generating a second ultrasound signal by the second ultrasound transducer array, wherein the second ultrasound signal is representative of the subject's anatomy along the second axis;

determining, by the logic circuit, an orientation of the ultrasound device with respect to the subject's anatomy based on the first ultrasound signal and the second ultrasound signal;

determining, by the logic circuit, if the first axis is unaligned with the subject's anatomy based on the orientation; and activating, when the first axis is unaligned with the subject's anatomy, a directional indicator of the plurality of directional indicators based on the determined orientation such that the directional indicator that is activated is configured to provide an indication to a user to move a corresponding location of the housing in a direction that the directional indicator points to align the first axis with the subject's anatomy.

14. The method of claim 13, wherein the first axis is orthogonal to the second axis.

15. The method of claim 13, wherein the generating the first ultrasound signal includes beamforming a plurality of ultrasound echo signals received from the first ultrasound transducer array.

16. The method of claim 13, further comprising:
determining at least one of Doppler measures or intensity measures based on the first ultrasound signal and the second ultrasound signal; and
determining the orientation based on the at least one of Doppler measures or intensity measures.

17. The method of claim 13, wherein the plurality of directional indicators comprise an arrow.

18. The method of claim 13,
wherein the at least one circuit board comprises one or more alignment indicators different than the plurality of directional indicators,
wherein the subject's anatomy includes a blood vessel,
wherein the method further comprises:
determining that the first axis of the ultrasound device is aligned with an axis of blood flow in the blood vessel; and
indicating, via the one or more alignment indicators, an alignment completion in response to determining that the first axis of the ultrasound device is aligned with the axis of blood flow in the blood vessel,
wherein the one or more alignment indicators comprise at least one of a light, a triangular shape, or a graphical line.

19. The method of claim 13, further comprising:
transmitting the first ultrasound signal and the second ultrasound signal to a remote device; and
displaying an image of the subject's anatomy based on at least one of the first ultrasound signal or the second ultrasound signal.

* * * * *